United States Patent
Leirens (10) Patent No.: US 11,162,971 B2
(45) Date of Patent: Nov. 2, 2021

(54) METHOD FOR DETECTING ACCELERATION PEAKS WITH NON-UNIFORM SAMPLING

(71) Applicant: COMMISSARIAT À L'ÉNERGIE ATOMIQUE ET AUX ÉNERGIES ALTERNATIVES, Paris (FR)

(72) Inventor: Sylvain Leirens, Grenoble (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 178 days.

(21) Appl. No.: 16/359,236

(22) Filed: Mar. 20, 2019

(65) Prior Publication Data

US 2019/0293678 A1   Sep. 26, 2019

(30) Foreign Application Priority Data

Mar. 21, 2018   (FR) ...................................... 1852448

(51) Int. Cl.
   *G01P 15/00* (2006.01)
   *G01C 21/10* (2006.01)
   *H03M 1/12* (2006.01)
   *A61B 5/11* (2006.01)

(52) U.S. Cl.
   CPC .............. *G01P 15/00* (2013.01); *G01C 21/10* (2013.01); *H03M 1/1275* (2013.01); *A61B 5/1123* (2013.01)

(58) Field of Classification Search
   CPC .... G01P 15/00; A61B 5/1123; H03M 1/1275; H03M 1/1265; G01C 21/10
   See application file for complete search history.

(56) References Cited

U.S. PATENT DOCUMENTS

| | | | | |
|---|---|---|---|---|
| 10,024,757 | B1* | 7/2018 | Niehues | G01M 7/025 |
| 2008/0238423 | A1 | 10/2008 | Bin et al. | |
| 2012/0257698 | A1 | 10/2012 | Li et al. | |
| 2013/0090881 | A1* | 4/2013 | Janardhanan | G06F 1/163 |
| | | | | 702/104 |
| 2014/0330535 | A1* | 11/2014 | Van Den Heuvel | B66B 5/0006 |
| | | | | 702/141 |
| 2014/0358472 | A1* | 12/2014 | Goel | A61B 5/1118 |
| | | | | 702/141 |
| 2015/0112218 | A1* | 4/2015 | Shani | A61B 5/352 |
| | | | | 600/516 |

(Continued)

OTHER PUBLICATIONS

Search Report for French application No. 1852448 dated Jan. 3, 2019.

(Continued)

*Primary Examiner* — Catherine T. Rastovski
*Assistant Examiner* — Aeysha N Sultana
(74) *Attorney, Agent, or Firm* — Pearne & Gordon LLP (57) ABSTRACT

A method for determining information regarding the displacement of an object from measurements provided by an accelerometer associated with the object. The method comprises the steps of detecting acceleration peaks in the measurements, of calculating one or more characteristics of the acceleration peaks detected, and of determining a mode of travel of the object from the characteristics of the acceleration peaks. The measurements undergo non-uniform resampling upon the detection of local extrema.

13 Claims, 5 Drawing Sheets

(56) References Cited

U.S. PATENT DOCUMENTS

| | | | |
|---|---|---|---|
| 2016/0327397 A1* | 11/2016 | Cordova | G06Q 40/08 |
| 2017/0000384 A1* | 1/2017 | Annegarn | G06K 9/0053 |
| 2017/0063475 A1* | 3/2017 | Feng | A61B 5/7278 |
| 2017/0122769 A1 | 5/2017 | Martin | |
| 2019/0110162 A1 | 4/2019 | Pereira Da Silva et al. | |
| 2019/0110272 A1 | 4/2019 | Pereira Da Silva et al. | |

OTHER PUBLICATIONS

Hemminki, Samuli et al. "Accelerometer-Based Transportation Mode Detection on Smartphones" IN: Proceedings of the 11th ACM Conference on Embedded Networked Sensor Systems, 2013, pp. 1-14.

"Nonuniform sampling", Wikipedia, Dec. 8, 2006.

U.S. Appl. No. 16/272,322 entitled "Calibration Method for a Triaxial Sensor With Selection of a Calibration Method as a Function of the Spatial Distribution of Measurements" filed Feb. 11, 2019.

* cited by examiner

METHOD FOR DETECTING ACCELERATION PEAKS WITH NON-UNIFORM SAMPLING

TECHNICAL FIELD

The field of the invention is that of determining information regarding the displacement of an object from measurements provided by an accelerometer. The invention more particularly relates to the automatic recognition of a mode of travel of the object by means of detecting acceleration peaks and of characterising these peaks in order to identify an acceleration profile typical of a transportation mode.

PRIOR ART

A known method of automatically identifying the transportation mode used by a user of a smartphone mobile terminal involves identifying an acceleration profile (duration, amplitude and frequency of the acceleration peaks) characteristic of a transportation mode. Reference can be made, for example, to the article by S. Hemminki, P. Nurmi, and S. Tarkoma, "Accelerometer-based transportation mode detection on smartphones", Proceedings of the 11th ACM Conference on Embedded Networked Sensor Systems 2013, pp. 1-14, which proposes detecting acceleration peaks by exceeding a threshold for the horizontal acceleration norm.

Such an approach requires obtaining measurements from an accelerometer over relatively long time windows, which can last as long as several minutes, in order to differentiate between a subway journey and a tram journey. However, embedded systems generally have a limited storage capacity.

DESCRIPTION OF THE INVENTION

The purpose of the invention is to propose a method allowing for the data useful for extracting the characteristics of the acceleration peaks to be compressed, without deteriorating the performance of the automatic recognition of the mode of travel. For this purpose, it proposes a method for determining information regarding the displacement of an object from measurements provided by an accelerometer associated with the object. The method comprises steps of detecting acceleration peaks in the measurements, of calculating one or more characteristics of the acceleration peaks detected, and of determining a mode of travel of the object from the one or more calculated characteristics. The method comprises, before the step of detecting acceleration peaks, a step of non-uniformly sampling the measurements. The step of non-uniformly sampling the measurements comprises a regular sampling of the measurements, the detection of local extrema in the measurements regularly sampled and a non-uniform resampling carried out to keep the local extrema.

Some preferred, however non-limiting aspects of said method are as follows:
- the non-uniform resampling is furthermore carried out in order to keep a sample when the duration separating said sample from a previously kept sample is greater than a time threshold;
- the non-uniform resampling is furthermore carried out in order to keep a sample when the amplitude variation between said sample and a previously kept sample is greater than an amplitude threshold;
- the non-uniform resampling is furthermore carried out in order to keep randomly selected samples;
- the detection of local extrema is carried out on a sliding-window covering a plurality of successive samples;
- the detection of local extrema further comprises storing the extremum type of the last extremum detected in memory;
- the detection of local extrema comprises correlating regularly sampled samples with one or more predetermined waveforms, and detecting a local extremum in the case wherein a correlation peak is identified;
- the step of detecting the acceleration peaks comprises determining a direction of travel of the object, determining an acceleration peak detection threshold from the non-uniformly sampled measurements projected in the direction of travel of the object and comparing the amplitude of the non-uniformly sampled measurements with the acceleration peak detection threshold;
- the determination of the acceleration peak detection threshold comprises calculating the variance of the non-uniformly sampled measurements;
- it further comprises comparing the amplitude of the non-uniformly sampled measurements with a noise threshold and an acceleration peak is formed of successive non-uniformly sampled measurements, the amplitude whereof is greater than the noise threshold and which include at least one measurement, the amplitude whereof is greater than the peak detection threshold;
- the step of calculating one or more characteristics of the detected acceleration peaks comprises determining at least one characteristic from the following group of characteristics: mean amplitude, mean duration and frequency.

BRIEF DESCRIPTION OF THE FIGURES

Other aspects, purposes, advantages and characteristics of the invention will be better understood upon reading the following detailed description given of non-limiting preferred embodiments of the invention, provided for illustration purposes, with reference to the accompanying figures, in which.

DETAILED DESCRIPTION OF SPECIFIC EMBODIMENTS

The invention relates to a method for determining information regarding the displacement of an object from measurements provided by an accelerometer associated with the object. The object can be a mobile terminal of a user, for example a smartphone.

The method according to the invention comprises the steps of detecting acceleration peaks in the measurements, of calculating one or more characteristics of the acceleration peaks detected, and of determining a mode of travel of the object from the one or more calculated characteristics. The invention proposes, before the step of detecting acceleration peaks, implementing a step of non-uniformly sampling the measurements.

The step of non-uniformly sampling the measurements can comprise a regular sampling of the measurements, the detection of local extrema in the measurements regularly sampled and a non-uniform resampling carried out to keep the local extrema.

According to the example embodiment showing the method according to the invention, an accelerometer of the three-axis sensor type is used and the measurements produced by said accelerometer are thus three-dimensional (three acceleration components). In a first embodiment, the axis of maximum variance can be determined and the detection of local extrema can be carried out in the acceleration component corresponding to this axis of maximum variance. In a second embodiment, the detection of local extrema can be carried out in each of the three acceleration components, whereby the detection of a local extremum in one of the components results in resampling from the other two components. This second embodiment results in a higher number of samples.

Other conditions can be added in order to resample more points, in particular random sampling or sufficient elapsed time or sufficient signal variation conditions. Thus, non-uniform resampling can furthermore be carried out in order to keep a sample when the duration separating said sample from a previously kept sample is greater than a time threshold $\Delta t^{max}$. It can also be carried out in order to keep a sample when the amplitude variation between said sample and a previously kept sample is greater than an amplitude threshold $\Delta x^{max}$. Lastly, it can also be carried out to keep randomly selected samples.

The detection of local extrema can be carried out on a sliding-window covering a plurality of successive samples of the acceleration measurements and can comprise the calculation of one or more growth rates between samples in the window.

Figure 1:
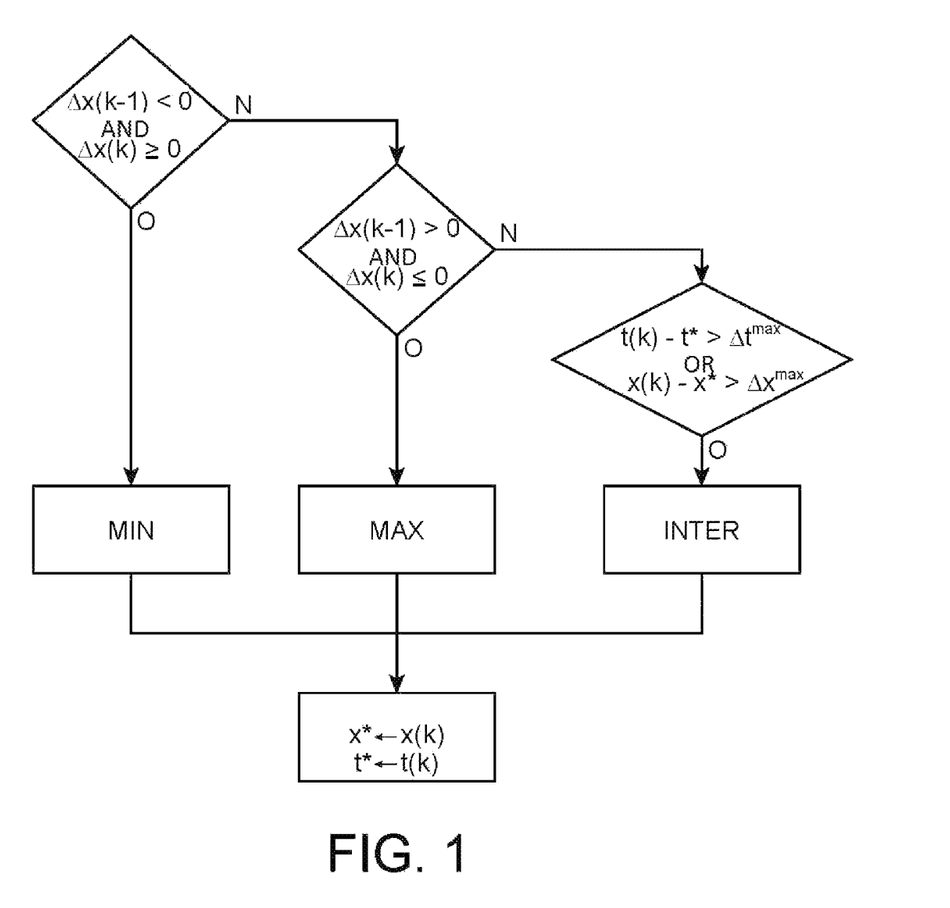
FIG. 1 shows non-uniform sampling criteria that can be implemented in the invention.

Let's consider an acceleration component x sampled at times t(k) referenced by the index k. The detection of the local extrema is, for example, carried out from a sliding-window covering three successive samples k−1, k and k+1. The successive growth rates $\Delta x(k-1)=x(k)-x(k-1)$ and $\Delta x(k)=x(k+1)-x(k)$ are calculated in order to determine whether the central sample k is at the apex of a triangle formed by the three samples and thus constitutes a local extremum. More particularly, as shown in FIG. 1, if $\Delta x(k-1)<0$ and $\Delta x(k)>0$, then the sample k is a local minimum MIN and if $\Delta x(k-1)>0$ and $\Delta x(k)<0$, then the sample k is a local maximum MAX. When a local extremum is thus detected, the amplitude thereof and the time thereof can be stored in memory as x* and t* respectively in order to allow the resampling to be carried out under sufficient elapsed time and signal variation conditions. Moreover, as shown in FIG. 1, if $t(k)-t^*>\Delta t^{max}$ or if $(k)-x^*>\Delta x^{max}$, then the sample k is referenced as an intermediate sample INTER and is included in the resampling, the amplitude thereof and the time thereof are stored in memory.

Moreover, a threshold concerning a minimum duration between two samples $\Delta t^{min}$ can be adopted, and/or a threshold concerning a minimum amplitude between two samples $\Delta x^{min}$ can be adopted so as not to trigger resampling as long as the duration that has lapsed since the last sample stored in memory is less than $\Delta t^{min}$ and/or as long as the variation in signal amplitude has not reached $\Delta x^{min}$.

In one possible embodiment, the detection of local extrema further comprises storing the extremum type of the last detected extremum in memory, i.e. whether it is a local maximum or minimum. In this manner, only a single growth rate $\Delta x(k)=x(k+1)-x(k)$ must be calculated. More specifically, a maximum (or respectively a minimum) is identified in the sample k if the last identified extremum is a minimum (or respectively a maximum) and if the growth rate is negative (or respectively positive).

In one alternative embodiment, the detection of local extrema comprises correlating regularly sampled samples with one or more predetermined waveforms, and detecting a local extremum in the case wherein a correlation peak is identified. The one or more waveforms are typically representative of the forms of the acceleration peaks expected for the different transportation modes.

Once resampling has been carried out, the method according to the invention implements a step of detecting acceleration peaks from the non-uniformly sampled measurements.

This step of detecting acceleration peaks comprises determining a direction of travel of the object. Let's suppose that M samples result from the non-uniform sampling. The gravity is estimated by calculating the mean of the signal in the time window:

$$\hat{g} = \frac{1}{M}\sum_{i=1}^{M} a_m(i),$$

where $\alpha_m(i)$ is the i-th resampled sample of the acceleration measurement (three-dimensional). By deducting the estimated gravity from the measured acceleration, an estimation of the natural acceleration of the object is obtained: $\hat{\alpha}(i)=\alpha_m(i)-\hat{g}$.

The direction of the movement can thus be determined by performing a principal component analysis of the natural acceleration $\hat{\alpha}$ and by assuming that the direction of the movement is that of maximum variance.

Figure 2A:
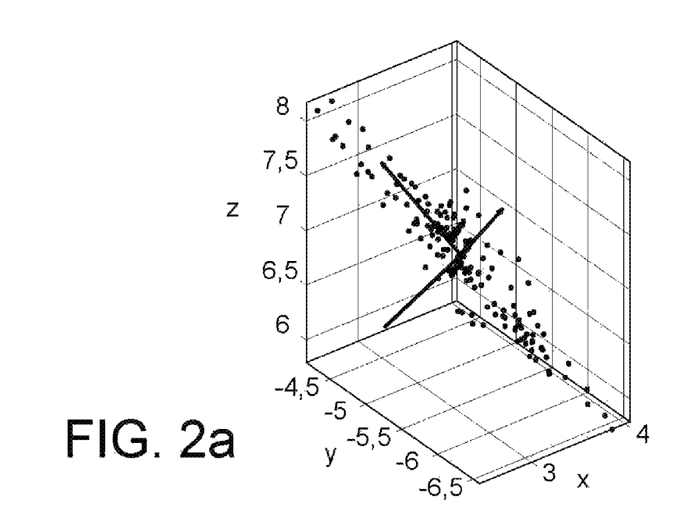
FIGS. 2a and 2b show the outcome of a principal component analysis carried out in order to search for the direction of the movement, respectively from the natural acceleration and the horizontal acceleration.
Figure 2B:
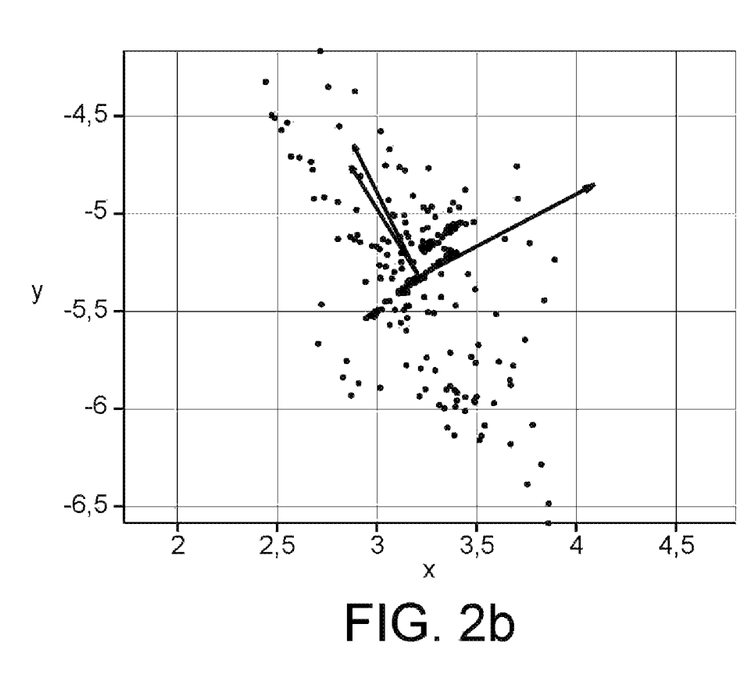

In order to carry out this principal component analysis, the natural acceleration $\hat{\alpha}$ is firstly projected in the horizontal plane, in other words, the vertical component is deducted from the natural acceleration: $\alpha_h(i)=\hat{\alpha}(i)-\hat{\alpha}(i)^T v$, where v is a unit vector that is the opposite of $\hat{g}$ (i.e. $v=-\hat{g}/\|\hat{g}\|$). If the horizontal acceleration $\alpha_h$ is a three-dimensional vector, the samples thereof are contained within a two-dimensional sub-space (i.e. contained within the horizontal plane). A principal component analysis of the horizontal acceleration is carried out. The direction of maximum variance $h_1$ is given by the eigenvector corresponding to the maximum eigenvalue of the correlation matrix of the horizontal acceleration (3×3 matrix). FIGS. 2a and 2b show the outcome of a principal component analysis carried out in order to search for the direction of the movement, respectively from the natural acceleration and the horizontal acceleration.

This analysis is based on the estimation of the gravity, which can be problematic. The hypothesis that the natural acceleration is zero on average in the time window is not always easy to meet in practice. One alternative approach is to carry out the principal component analysis on the measured acceleration $\alpha_m$. The problem of estimating the gravity is avoided, however the hypothesis that the direction of the movement is that of maximum variance is more difficult to verify, especially in the presence of noise or vibrations (in particular along the vertical axis).

Once the direction of the movement has been identified to be along the first principal axis $h_1$, the horizontal acceleration (or the natural acceleration depending on the chosen method) is projected along $h_1$ in order to obtain a longitudinal acceleration $\alpha_{h1}$ corresponding to the non-uniformly sampled measurements projected in the direction of travel of the object. The step of detecting the acceleration peaks is continued by determining, from the longitudinal acceleration $\alpha_{h1}$, an adaptive acceleration peak detection threshold. The determination of this threshold can in particular comprise the calculation of the variance in the non-uniformly sampled measurements.

In order to simplify the nomenclature, the longitudinal acceleration $\alpha_{h1}$ has been renamed x. The sample variance $\sigma^2$ in a window of M samples of an irregularly-sampled signal x is calculated as follows:

$$\sigma^2 = \frac{1}{t(M) - t(1)} \sum_{i=2}^{M} (x(i) - \mu)^2 (t(i) - t(i-1))$$

where the empirical mean $\mu$ is given by:

$$\mu = \frac{1}{t(M) - t(1)} \sum_{i=2}^{M} x(i)(t(i) - t(i-1))$$

The acceleration peak detection threshold can be calculated based on the full width at half maximum H of the normal distribution that is proportional to $\sigma$: $H = 2\sqrt{2\ln 2}\ \sigma$, and the threshold s is taken to be equal to half of H: $s = H/2$.

Figure 3:
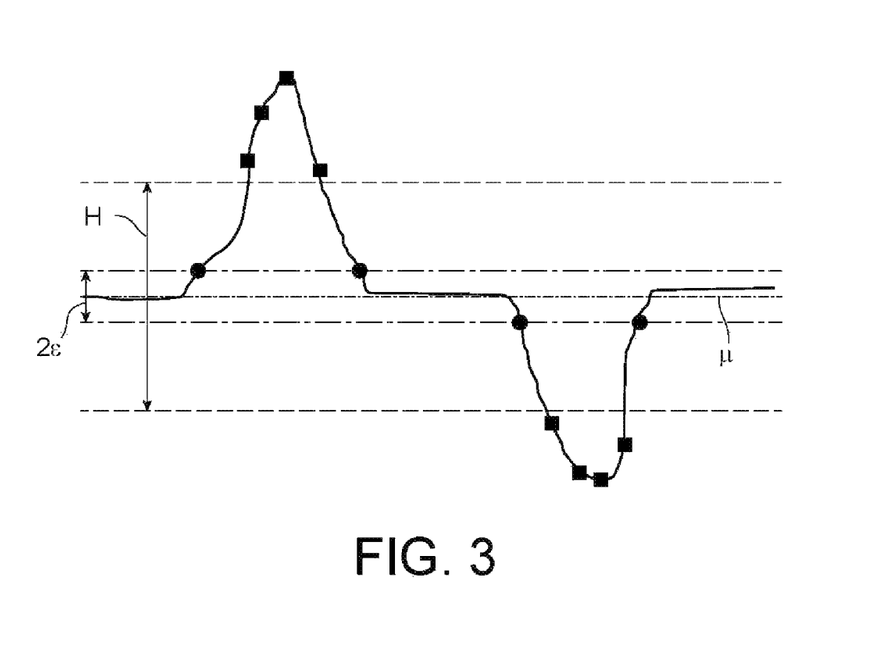
FIG. 3 shows the detection and delimitation of an acceleration peak.

FIG. 3 shows the detection and delimitation of an acceleration peak. The detection of an acceleration peak comprises comparing the amplitude of the non-uniformly sampled measurements with the acceleration peak detection threshold s and identifies the samples located outside of the width area H (samples shown by squares in FIG. 3.)

The delimitation of an acceleration peak comprises comparing the amplitude of the non-uniformly sampled measurements with a noise threshold E. An acceleration peak is thus formed of successive non-uniformly sampled measurements, the amplitude whereof is greater than the noise threshold E and which include at least one measurement, the amplitude whereof is greater than the peak detection threshold s. The use of a noise threshold makes the delimitation of the acceleration peaks resistant to noise.

As shown in FIG. 3, the noise threshold E can be a tolerance around the empirical mean $\mu$, for example 0.1 m/s². The start and end of a peak are thus determined by searching for the samples situated the closest to the width area 2E around the sample empirical $\mu$ (samples shown by circles in FIG. 3).

Once the acceleration peaks have been detected and delimited, the method comprises calculating one or more characteristics of each acceleration peak in order, for example, to automatically classify the transportation modes. For example, at least one characteristic of the following group of characteristics is determined: mean amplitude, mean duration and frequency of the acceleration peaks. The automatic classification can be carried out by means of algorithms such as decision trees or random forests.

The invention is not limited to the method as described hereinabove, but also extends to a computer program comprising instructions for carrying out this method when said program is executed on a computer. The invention further extends to a device, for example to a device embedded within a mobile terminal of a user, comprising a data processing unit configured to implement this method.

It can be seen from the above description that the invention in particular proposes resampling upon the detection of extrema of the axis of maximum variance or coupled over the three axes. For more reliability, this resampling can be enhanced with the detection of thresholds and/or by random sampling. The invention further proposes estimating the longitudinal acceleration and calculating characteristics of the longitudinal acceleration profile by means of the detection of acceleration peaks by exceeding an adaptive threshold. The invention thus has the advantage of allowing a data compression that suits the content. It does not require reconstruction of the signal in order to extract the characteristics, is simple to implement, and can undergo simple configurations.

The paragraphs below present two example embodiments of the invention. In each of these examples, the following configurations are used: $\Delta t^{max} = 5$ s, $\Delta x^{max} = 0.2$ m/s², $\Delta t^{min} = 0$ s and $\Delta x^{min} = 0.02$ m/s².

The first example corresponds to a journey by subway. The sampling frequency of the three-axis accelerometer is 100 Hz, the time window considered is 60 seconds, the number of samples is 6000 and a low-pass filtering with a 2 Hz cut-off frequency at −3 dB is carried out on the actual measurements provided by the accelerometer.

Figure 4A:
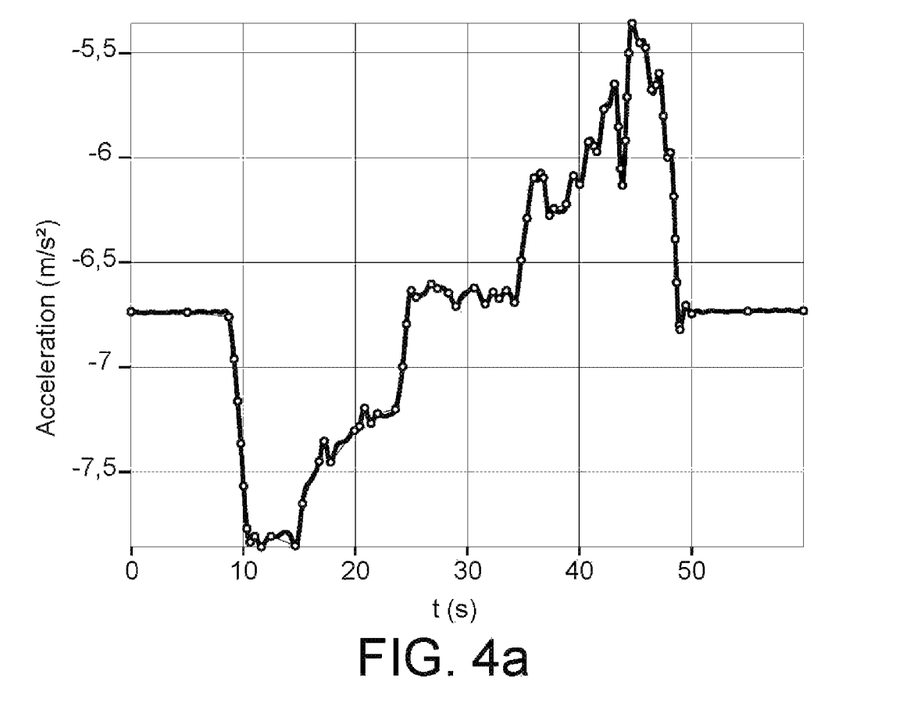
FIGS. 4a and 4b respectively show the non-uniform sampling and the detection of acceleration peaks according to the invention in one example of travelling by subway.
Figure 4B:
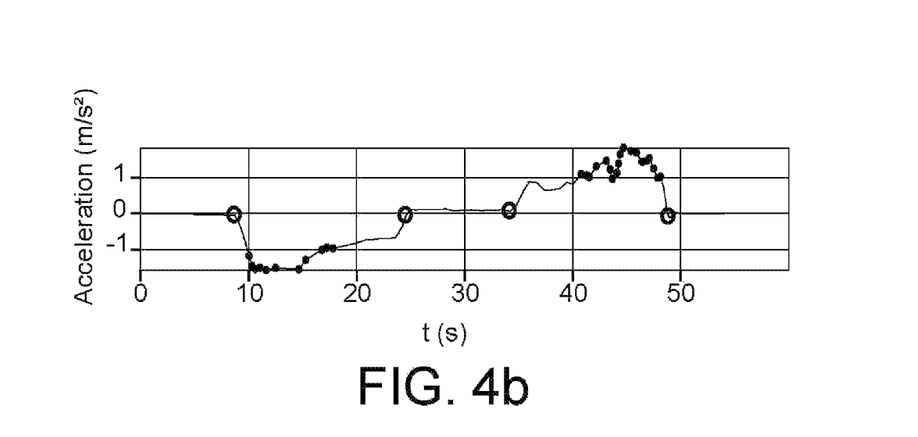

FIG. 4a shows the non-uniform resampling of the component of the accelerometer signal corresponding to the axis of maximum variance. 76 samples are kept, and the mean resampling frequency is 1.25 Hz. FIG. 4b shows the detection of the acceleration peaks. The detection threshold calculated according to the example embodiment presented hereinabove is equal to 0.924 m/s². The mean amplitude of the two peaks detected (mean amplitude of the samples above the detection threshold for positive amplitudes and mean amplitude of the samples below the opposite of the detection threshold for negative amplitudes) is 1.01 m/s² and −1.04 m/s², to be compared with reference amplitudes of 1.02 m/s² and −1.05 m/s², as calculated with regular sampling. The durations of the peaks detected is 15.7 s and 14.4 s, to be compared with reference durations of 15.6 s and 14.3 s, as calculated with regular sampling. The frequency of the peaks detected is 0.0333 Hz, i.e. 2.0 min$^{-1}$, to be compared with a reference frequency of 2.0 min$^{-1}$, as calculated with regular sampling.

The second example corresponds to a journey by car. The sampling frequency of the three-axis accelerometer is 86.5 Hz, the time window considered is 30 s, the number of samples is 2566 and a low-pass filtering with a 2 Hz cut-off frequency at −3 dB is carried out on the actual measurements provided by the accelerometer.

Figure 5A:
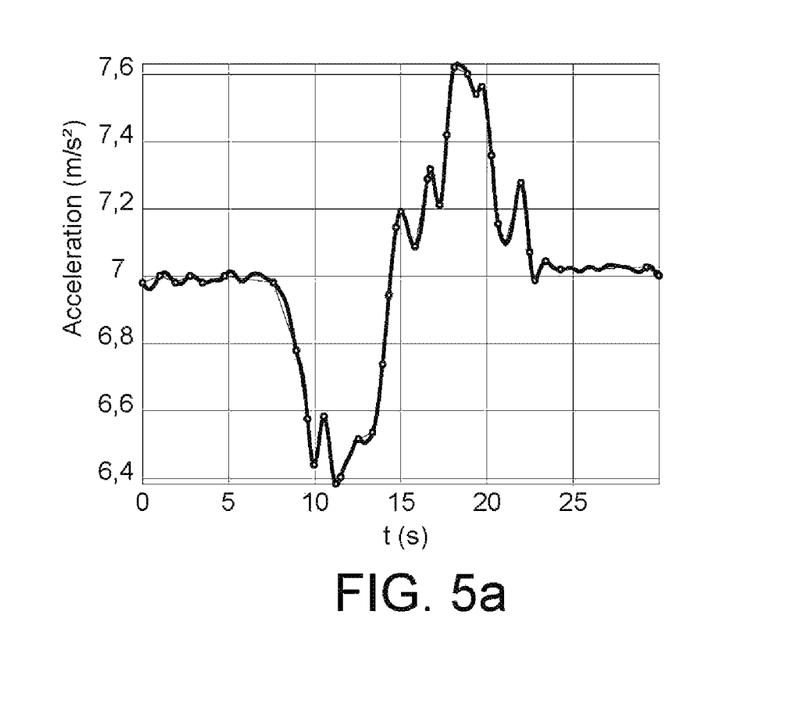
FIGS. 5a and 5b respectively show the non-uniform sampling and the detection of acceleration peaks according to the invention in one example of travelling by car.
Figure 5B:
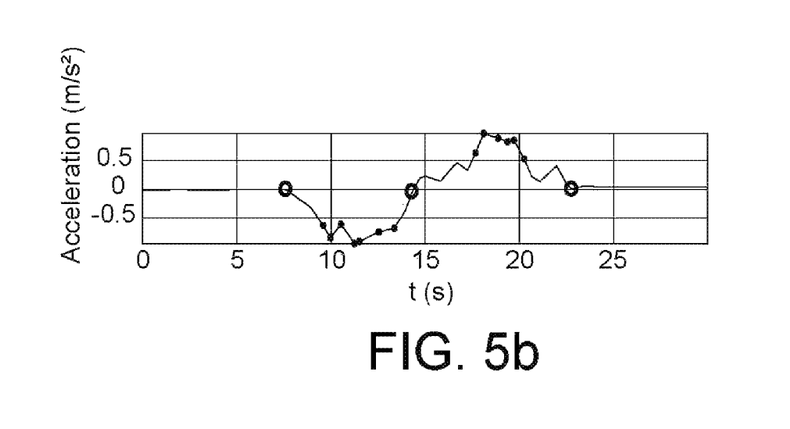

FIG. 5a shows the non-uniform resampling of the component of the accelerometer signal corresponding to the axis of maximum variance. 39 samples were kept, and the mean resampling frequency was 1.26 Hz. FIG. 5b shows the detection of the acceleration peaks. The detection threshold calculated according to the example embodiment presented hereinabove is equal to 0.490 m/s². The mean amplitude of the two peaks detected is −0.60 m/s² and 0.44 m/s², to be compared with reference amplitudes of −0.63 m/s² and 0.46 m/s², as calculated with regular sampling. The durations of the peaks detected is 6.24 s and 7.95 s, to be compared with reference durations of 6.04 s and 7.97 s, as calculated with regular sampling. The frequency of the peaks detected is 0.0667 Hz, i.e. 4.0 min$^{-1}$, to be compared with a reference frequency of 4.0 min$^{-1}$, as calculated with regular sampling.

What is claimed is:

1. A method for determining information regarding the displacement of an object, comprising the steps of:

non-uniformly sampling of measurements provided by an accelerometer associated with the object, the non-uniformly sampling comprising:
   a regular sampling of measurements,
   a detection of local extrema in the regularly sampled measurements, and
   a non-uniform resampling of the measurements carried out to keep the detected local extrema,
detecting acceleration peaks in the measurements provided by the accelerometer associated with the object,
calculating one or more characteristics of the detected acceleration peaks, and
determining a mode of travel of the object from the one or more calculated characteristics, wherein the step of non-uniformly sampling the measurements is performed before the step of detecting the acceleration peaks.

2. The method according to claim 1, wherein the non-uniform resampling is furthermore carried out in order to keep a sample when a duration separating said sample from a previously kept sample is greater than a time threshold.

3. The method according to claim 1, wherein the non-uniform resampling is furthermore carried out in order to keep a sample when an amplitude variation between said sample and a previously kept sample is greater than an amplitude threshold.

4. The method according to claim 1, wherein the non-uniform resampling is furthermore carried out in order to keep randomly selected samples.

5. The method according to claim 1, wherein the detection of local extrema is carried out from a sliding-window covering a plurality of successive samples.

6. The method according to claim 5, wherein the detection of local extrema further comprises storing the extremum type of the last extremum detected in memory.

7. The method according to claim 1, wherein the detection of local extrema comprises correlating the regularly sampled samples with one or more predetermined waveforms, and detecting a local extremum when a correlation peak is identified.

8. The method according to claim 1, wherein the step of detecting the acceleration peaks comprises determining a direction of travel of the object, determining an acceleration peak detection threshold from the non-uniformly sampled measurements projected in the direction of travel of the object and comparing the amplitude of the non-uniformly sampled measurements with the acceleration peak detection threshold.

9. The method according to claim 8, wherein the determination of the acceleration peak detection threshold comprises calculating the variance of the non-uniformly sampled measurements.

10. The method according to claim 8, further comprising comparing the amplitude of the non-uniformly sampled measurements with a noise threshold and wherein an acceleration peak is formed of successive non-uniformly sampled measurements, the amplitude whereof is greater than the noise threshold, and includes at least one measurement, the amplitude whereof is greater than the acceleration peak detection threshold.

11. The method according to claim 1, wherein the step of calculating one or more characteristics of the detected acceleration peaks comprises determining at least one characteristic from the following group of characteristics: mean amplitude, mean duration and frequency.

12. A computer program comprising instructions for executing the method according to claim 1, when said program is executed on a computer.

13. A device comprising a data processing unit configured to implement the method according to claim 1.

* * * * *